United States Patent [19]
Iijima et al.

[11] Patent Number: 5,972,879
[45] Date of Patent: Oct. 26, 1999

[54] INHIBITING AGENT AGAINST THE PROLIFERATION OF TUMOR CELLS

[75] Inventors: Kunihito Iijima, Tokyo; Haruki Kato, Hanno; Yoichiro Nagasu, Yamato, all of Japan

[73] Assignee: Koken Co., Ltd., Tokyo, Japan

[21] Appl. No.: 07/700,158

[22] PCT Filed: Dec. 21, 1990

[86] PCT No.: PCT/JP90/01678

§ 371 Date: May 14, 1991

§ 102(e) Date: May 14, 1991

[87] PCT Pub. No.: WO91/09612

PCT Pub. Date: Jul. 11, 1991

[30] Foreign Application Priority Data

Dec. 25, 1989 [JP] Japan .................................... 1-332870

[51] Int. Cl.[6] .......................... A61K 38/00; A61K 38/02
[52] U.S. Cl. ................................................................. 514/2
[58] Field of Search .................................................. 514/2

[56] References Cited

U.S. PATENT DOCUMENTS 4,211,769  7/1980  Okada et al. ............................ 424/177

FOREIGN PATENT DOCUMENTS 0 127 426  12/1984  European Pat. Off. ................... 514/2

OTHER PUBLICATIONS

Patent Astracts of Japan, vol. 9, No. 130, (C–284) (1853) dated Jun. 5, 1985.

*Primary Examiner*—Avis M. Davenport
*Attorney, Agent, or Firm*—McDermott, Will & Emery

[57] ABSTRACT

An inhibiting agent against the proliferation of tumor cells comprises a lower condensation polymer or oligomer of an α-hydroxy acid, an oligopeptide containing at least one pyroglutamic acid residue, and a stabilizer. The lower condensate and the lower polymer of an α-hydroxy acid comprise mainly compounds formed by condensing and polymerizing 2 to 10 molecules of an α-hydroxy acid and their metal salts. The weight ratio of the components is such that the ratio of the lower condensate and the lower polymer of an α-hydroxy acid is 10, the ratio of the oligopeptide containing at least one pyroglutamic acid residue is 1 to 4, and the ratio of the stabilizer a saccharide or a sugaralcohol comprising is 1 to 3.

2 Claims, 1 Drawing Sheet

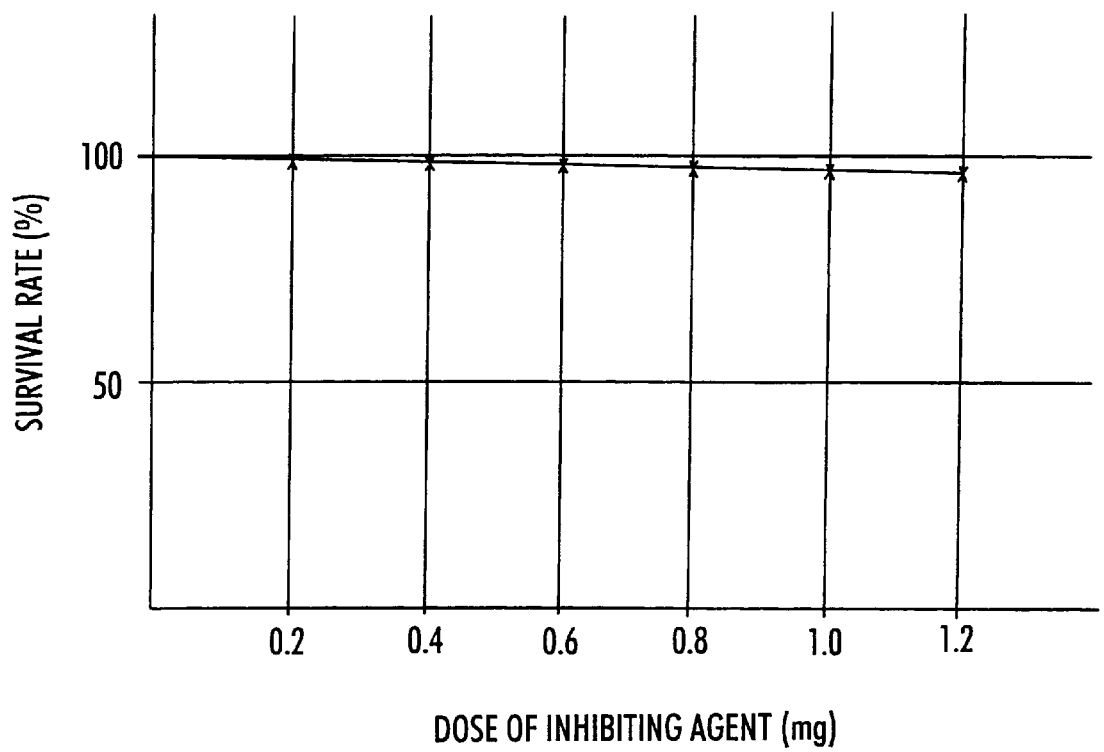

INHIBITING AGENT AGAINST THE PROLIFERATION OF TUMOR CELLS

TECHNICAL FIELD

The present invention relates to an inhibiting agent against the proliferation of tumor cells of animals including human beings.

BACKGROUND ART

In spite of the fact that the study of development of carcinostatics are being carried out energetically on a worldwide scale, none of currently used effective carcinostatics are employed without anxiety because of the side effects. Also, in view of the current state that, among physicotherapies, there is no effective and noticeable one that gives less load, it is desired to develop satisfactory carcinostatics as soon as possible.

Taking this into consideration, the present applicant suggested inhibiting agents against the proliferation of malignant tumor cells of human beings in U.S. Pat. Nos. 4,810,495 and 4,963,358 and a process for the preparation of an inhibiting agent against the proliferation of malignant tumor cells of animals in U.S. Pat. No. 4,595,657.

However, in those patents, the substances that inhibit the proliferation of malignant tumor cells were unclear.

Further, the present applicant suggested an inhibiting agent against the proliferation of malignant tumor cells of human beings comprising 2-hydroxy-1-(P-hydroxyphenyl)-5-methylhexane-3-one in Japanese Patent Tokkai-hei 2-247121 (Laid-Open No. 247121/1995), an inhibiting agent against the proliferation of malignant tumor cells of human beings comprising a monoglyceride in Japanese Patent Tokkai-hei 2-247125 (Laid-Open No. 247125/1995), and an inhibiting agent against the proliferation of malignant tumor cells of human beings comprising 2-heptadecanol in Japanese Patent Tokkai-hei 2-247120 (Laid-Open No. 247120/1995).

The object of the present invention is. to provide an inhibiting agent against the proliferation of tumor cells which is not any of the substances that were suggested in the above inventions, does not affect at all, in a toxicity test using normal cells, their proliferation, further in a test of the inhibition of proliferation of tumor cells of human beings transplanted in nude mice, stops the proliferation several days after the start of the administration as well as permits the tumor to reduce significantly in spite of the absence of followed administration, shows stable effectiveness by hypodermic administration, and has a stable prolonged action in organisms.

DISCLOSURE OF INVENTION

The present inhibiting agent against the proliferation of tumor cells comprises a lower condensation polymer or oligomer of an α-hydroxy acid, an oligopeptide containing at least one pyroglutamic acid residue, and a stabilizer.

Said lower condensation polymer or oligomers of an α-hydroxy acid are mainly those comprising compounds formed by condensing and polymerizing 2 to 10 molecules of an α-hydroxy acid and their metal salts.

Further, said oligopeptide containing at least one pyroglutamic acid residue comprises a compound containing at least one pyroglutamic acid residue that is an oligopeptide made up of 2 to 8 amino acid residues and its metal salt.

The weight ratio of the components is such that the ratio of the lower condensation polymer or oligomer of an α-hydroxy acid is 10, the ratio of the oligopeptide containing at least one pyroglutamic acid residue is 1 to 4, and the ratio of the stabilizer (a saccharide or a sugaralcohol) is 1 to 3.

BRIEF DESCRIPTION OF THE DRAWING

FIG. 1 is a chart showing the relationship of the survival rates to the doses of the present inhibiting agent against the proliferation of tumor cells

BEST MODE FOR CARRYING-OUT THE INVENTION

EXAMPLE 1

Preparation of Lactic Acid Oligomer (Condensation Polymer of β-Hydroxypropionic Acid)

Lactic acid (α-hydroxypropionic acid) is chemically highly reactive and solidifies when heated for 100 min at 140° C. When the solid is dissolved in water and is rendered alkaline, a precipitate is formed, which hardly dissolves even when it is rendered acid. When the precipitate is heated for 2 hours at 175° C., it turns into a substance that does not dissolve in water but dissolves in methanol. The requirement herein is that it is soluble in water and stable and the process for the preparation that satisfies the conditions are described below.

(1) 0.7 ml of 6N hydrochloric acid is added to 50 ml of L-lactic acid and the mixture is refluxed for 2 hours or is heated for 100 min at 120 to 160° C.

(2) 0.5 g of $NaHCO_3$ is dissolved in 50 ml of L-lactic acid, then 150 ml of toluene is added thereto, and the mixture is heated for 2 hours at 140 to 160° C.

(3) 2 ml of sodium lactate is added to 50 ml of L-lactic acid, then 100 ml of benzene is added, and the mixture is heated for 3 to 6 hours at 140° C.

(4) 0.2 g of $MgCl_2$ (or $CaCl_2$) and 150 ml of toluene are added to 50 ml of L-lactic acid and the mixture is refluxed for 2 to 4 hours.

By the above process, a compound comprising the condensation polymer of α-hydroxypropionic acid molecules was obtained.

EXAMPLE 2

The lower condensation polymer of α-hydroxypropionic acid described in the above Example, an oligopeptide containing at least one pyroglutamic acid residue, and a stabilizer comprising a saccharide or a sugaralcohol were mixed in a weight ratio of 10:1–4:1–3 and a small amount of a metal salt of α-hydrotypropionic acid as a catalyst was added thereto to prepare an inhibiting agent against the proliferation of tumor cells.

Results of Experiments
Experiment 1
Acute Toxicity Test

10 μl of each of the inhibiting agents containing respective doses was added to 990 μl of commercially available synthetic medium Eagle's MEN to which 10% fetal calf serum was added, each of them as a medium was added to a 15-mm diameter plastic 24-hole multi-plate implanted with $1\times10^5$ skin fibroblasts and after they were cultured at 37° C. for 72 hours in a $CO_2$ atmosphere, the uptake of methylene blue dye into the cells was measured in terms of the absorbance at a wavelength of 62.0 nm.

From the absorbance at that time, the survival rate was calculated. The relationship between the survival rates and the doses of the inhibiting agent is shown in Table 1 and the FIGURE.

TABLE 1

| Dose of inhibiting agent (mg) | 0.2 | 0.4 | 0.6 | 0.8 | 1.0 | 1.2 |
|---|---|---|---|---|---|---|
| Survival rate (%) | 99.9 | 99.0 | 98.5 | 98.0 | 97.4 | 96.2 |

Experiment 2

Experiment in inhibition of proliferation of malignant tumor cells (A) Method: $1\times10^7$ of established cell Hela S-3 cells originated from cervical carcinoma were transplanted in the dorsalis of each of nude mice (ICR NU/NU ♀; 5 weeks old), then from the fifth day after the transplantation, 20 mg of the inhibiting agent per 0.5 ml of $H_2O$ was administered to the experiment group once a day for ten days continuously and 0.5 ml of physiological saline was administered to the control group in a similar manner. Thereafter the administration was stopped and at the seventh week after the transplantation, the tumors were removed and weighed.

Dose: 20 mg/0.5 ml $H_2O$/administration

Way of administration: hypodermic administration (SC)

Results: The weights of tumors of 5 examples of each of the control group and the experiment group are shown in Table 2.

TABLE 2

| No. | Control group (g) | Experiment group (g) |
|---|---|---|
| 1 | 3.25 | 0.25 |
| 2 | 3.15 | 0.63 |
| 3 | 4.13 | 0.54 |
| 4 | 3.46 | 0.62 |
| 5 | 3.27 | 0.64 |
| Σx | 17.26 | 2.68 |
| $\bar{x}_1$ | $3.45_2$ | $0.53_6$ |

Inhibition Efficiency: 84.5%

The inhibition efficiency was determined in accordance with the following formula:

$$\left(1 - \frac{\text{weight of tumor of experiment group }(g)}{\text{weight of tumor of control group }(g)}\right) \times 100$$

(B) (A) was repeated, except that administration was effected ice a day, that is, the number of administrations was 20. The weights of tumors of 5 examples of each of the control group and the experiment group are shown in Table 3.

TABLE 3

| No. | Control group (g) | Experiment group (g) |
|---|---|---|
| 1 | 3.41 | 0.26 |
| 2 | 3.26 | 0.31 |
| 3 | 4.38 | 0.41 |
| 4 | 3.81 | 0.37 |
| 5 | 4.20 | 0.29 |

TABLE 3-continued

| No. | Control group (g) | Experiment group (g) |
|---|---|---|
| Σx | 19.06 | 1.00 |
| $\bar{x}$ | $3.82_1$ | $0.32_8$ |

Inhibition Efficiency: 91.4%

(C) Method: The same experiment as (A) was carried out, except that established cell MKN-1 cells originated from human gastric cancer were used.

Results: The weights of tumors of 5 examples of each of the control group and the experiment group are shown in Table 4.

TABLE 4

| No. | Control group (g) | Experiment group (g) |
|---|---|---|
| 1 | 5.04 | 0.73 |
| 2 | 4.41 | 0.55 |
| 3 | 5.67 | 0.81 |
| 4 | 4.90 | 0.69 |
| 5 | 4.93 | 0.67 |
| Σx | 24.95 | 3.45 |
| $\bar{x}$ | 4.99 | 0.69 |

Inhibition Efficiency: 86.2%

INDUSTRIAL APPLICABILITY

The present inhibiting agent against the proliferation of tumor cells is a low-molecular-weight derivative of a substance existing in organisms or a food additive and do not affect the proliferation of normal cells at all in a toxicity test using normal cells. Further in a test in inhibition of proliferation of malignant tumor cells transplanted in nude mice, after several days of the start of the administration of the inhibiting agent the proliferation was stopped and even without administering the inhibiting agent thereafter the tumors reduced significantly. When the present inhibiting agent is administered hypodermically, since it exhibits its effectiveness stably, it is a substance having a stable prolonged action in organisms. Thus, any side effect is not observed in the course of animal experiments and therefore the present inhibiting agent is suitable as an effective carcinostatic that can be used without anxiety.

We claim:

1. A composition, consisting essentially of (a) a lower condensation polymer or oligomer of an α-hydroxy acid, the condensation polymer or oligomer of an α-hydroxy acid being formed by condensing and polymerizing 2 to 10 molecules of an α-hydroxy acid or a metal salt of said acid, (b) an oligopeptide consisting essentially of a compound containing at least one pyroglutamic acid residue or its metal salt and 2 to 8 amino acid residues, and (c) a stabilizer comprising a saccharide or a sugar alcohol, the weight ratio of the components being such that the ratio of the lower condensation polymer or oligomer of an α-hydroxy acid is 10, the ratio of the oligopeptide containing at least one pyroglutamic acid residue is 1 to 4, and the ratio of the stabilizer is 1 to 3.

2. A composition as defined by claim 1, wherein the α-hydroxy acid is L-lactic acid.

* * * * *